United States Patent [19]

Warrington et al.

[11] Patent Number: 5,466,693
[45] Date of Patent: Nov. 14, 1995

[54] GRANULAR FUNGICIDAL COMPOSITION FOR APPLICATION TO AN AQUATIC ENVIRONMENT

[75] Inventors: Roger P. Warrington, Wokingham; Guy Ramsay, Bracknell, both of England; Neal R. Bird, Richmond, Calif.

[73] Assignee: Imperial Chemical Industries PLC, London, England

[21] Appl. No.: 125,702

[22] Filed: Sep. 23, 1993

Related U.S. Application Data

[63] Continuation of Ser. No. 570,588, Aug. 21, 1990, abandoned.

[30] Foreign Application Priority Data

Sep. 1, 1989 [GB] United Kingdom .................. 8919833
Apr. 9, 1990 [GB] United Kingdom .................. 9007995

[51] Int. Cl.⁶ .......................... A01N 43/54; A01N 25/12; A01N 25/14
[52] U.S. Cl. .......................... 514/269; 514/951; 514/952; 424/409; 424/502
[58] Field of Search .................... 514/269, 951, 514/952; 424/409, 502

[56] References Cited

U.S. PATENT DOCUMENTS

| | | | |
|---|---|---|---|
| 4,080,191 | 3/1978 | Harvey | 71/92 |
| 4,886,656 | 12/1989 | Obayashi et al. | 424/10 |
| 5,145,856 | 9/1992 | Clough et al. | 514/274 |

FOREIGN PATENT DOCUMENTS

| | | |
|---|---|---|
| 7166581 | 3/1985 | Australia . |
| 2008701 | 8/1990 | Canada . |
| 113857 | 7/1984 | European Pat. Off. . |
| 189377 | 7/1986 | European Pat. Off. . |
| 206987 | 12/1986 | European Pat. Off. . |
| 248554 | 12/1987 | European Pat. Off. . |
| 2611436 | 9/1988 | France . |
| 2611435 | 9/1988 | France . |
| 8817802 | 1/1988 | Japan . |
| 2184946 | 7/1987 | United Kingdom . |

OTHER PUBLICATIONS

The Merck Index, 10th Edition, Windholz, editor, Merck & Co., Inc, Rahway N.J., 1983, p. 980.
J55141401 (Nihon Noyaku KK) (Abstract only), Apr. 20, 1979.
J55154902 (Nippon Toketsu Kans) (Abstract only) May 23, 1979.
J56030901 (Nihon Noyaku KK) (Abstract only), Aug. 23, 1979.
J62188602 (Sankei Chemicals Company Limited) (Abstract only) Sep. 2, 1987.
J63041401 (Higashimura et al.) (Abstract only) Feb. 22, 1988.
J73015614 (Tokyo Organic Chemical Inds. Ltd.) (Abstract only) Feb. 14, 1970.
Chem. Abstracts 112:32163c (Walcerz et al.), 1990.
Chem. Abstracts 112:50640k (Puritch et al.), 1990.
Chem. Abstracts 112:50643p (Idemitsu Kosan Co., Ltd.), 1990.
Chem. Abstracts 103:208952q (Sekiguchi et al.), 1985.

*Primary Examiner*—Allen J. Robinson
*Assistant Examiner*—Brian G. Bembenick
*Attorney, Agent, or Firm*—Marian T. Thomson

[57] ABSTRACT

A fungicidal, herbicidal or plant growth regulating composition for application to an aquatic environment, the composition comprising a solid carrier, a fungicidal, herbicidal or plant growth regulating active ingredient, and an oil with which the said active ingredient is miscible or in which it is capable of being dispersed, said oil being water-immiscible, having a specific gravity of less than 1 and a boiling point at atmospheric pressure of greater than 150° C.

The compostitions are particularly useful for application to a paddy-field to assist in the cultivation of rice.

7 Claims, No Drawings

GRANULAR FUNGICIDAL COMPOSITION FOR APPLICATION TO AN AQUATIC ENVIRONMENT

This is a continuation of application Ser. No. 07/570,588, filed Aug. 21, 1990 (abandoned).

This invention relates to fungicidal, herbicidal and plant growth regulatory compositions for use in the application of fungicides, herbicides and plant growth regulators to aquatic environments and methods of use of and processes for preparing such compositions.

Oil releasing granules have been described for the application of insecticides to paddy-fields (see for example Japanese Kokai Nos 62-188602 and 63-17802).

Hitherto however fungicides, herbicides and plant growth regulators have been applied to paddy-fields in the form of soluble, dispersible or absorbent granules which release the active ingredient into the water, or by pour-on liquids, in particular emulsifiable concentrate formulations which disperse the active ingredient on the surface of the water (see for example EP-A-206987).

According to the present invention there is provided a fungicidal, herbicidal or plant growth regulating composition for application to an aquatic environment the composition comprising a solid carrier, a fungicidal, herbicidal or plant growth regulating active ingredient, and an oil with which the said active ingredient is miscible or in which it is capable of being dispersed, said oil being water-immiscible, having a specific gravity of less than 1 and a boiling point at atmospheric pressure of greater than 150° C.

Compositions according to the present invention when applied to aquatic environments such as paddy-fields, waterways for example streams, rivers and canals, and reservoirs, release active ingredient in solution or dispersion in the oil which, because of its low specific gravity, rises to the surface of the water to form an oily film. The oily film may subsequently spread over the stems and leaves of the plants present, and where this happens, plant uptake of the active ingredient may be aided. By floating on the water surface the oily film, and hence the active ingredient, is substantially kept away from the soil zone and the roots of the plants. The fact that active ingredients are substantially kept away from the soil zone may be particularly useful for example where such compounds show a degree of persistence in the soil.

Hence in further aspects of the invention there are provided methods for controlling fungal growth on plants growing in an aquatic environment, for killing or controlling unwanted plants in an aquatic environment and for regulating the growth of plants growing in an aquatic environment, which methods comprise applying to the aquatic environment an effective amount of an appropriate composition of the invention.

Most preferably the aquatic environment is a paddy-field where the compositions can be used to control fungal growth on rice plants, regulate the growth of the rice plant or control unwanted weeds found in a paddy-field, depending upon the active ingredient employed.

In a preferred embodiment, the compositions according to the invention are in the form of granules.

Granular compositions are easy to handle, store and apply, and by releasing their active ingredient at the point of application only allow for controlled distribution avoiding undesired drift.

Suitable solid carriers may be soluble, insoluble, or dispersible in water, or mixtures of these provided that when they are applied to water, they allow the release of the solution or dispersion of the active ingredient into the water. This will usually be effected by the break-up or dissolution of the solid carrier.

Examples of soluble carriers include alkali metal, magnesium or ammonium salts of inorganic and organic acids, for example the sodium, potassium, magnesium or ammonium salts of hydrochloric acid, sulphuric acid, nitric acid or acetic acid, sodium carbonate, sodium sesquicarbonate, sugars, and mono- and di-saccharides such as lactose or sucrose, or water-soluble polymers. Suitable water dispersible or water-insoluble carriers include clay, talc, calcium carbonate, diatomaceous earth, white carbon, kaolin, bentonite, starch, kieselguhr, glass powder, pumice, sand and brick fragments.

The granules may additionally contain effervescence-initiating components in order to ensure rapid release of the active ingredient solution from the granule. Examples of effervescence-initiating components are described in GB-2,184,946-A. They include conventional effervescent couples, for example, a solid acid and a carbonate or bicarbonate such as an alkali metal carbonate or bicarbonate. Examples of suitable acids include citric acid, malic acid, alginic acid, adipic acid, benzoic acid, phthalic acid, succinic acid, o-toluic acid, salicylic acid, and o-chlorobenzoic acid. Examples of suitable carbonates or bicarbonates include sodium hydrogen carbonate, sodium bicarbonate and sodium sesquicarbonate. For instance, suitable effervescent pairs include citric or malic acid combined with sodium bicarbonate or adipic acid combined with sodium sesquicarbonate. Preferably the effervescent couples are present in a ratio of from 3:1 to 1:1 of acid:carbonate or bicarbonate, preferably in a ratio of 2:1.

The amount of active ingredient contained within the composition will vary depending upon the nature of the active ingredient as well as the other components of the composition. However in general the formulations will contain from 0.01 to 200 g/kg of active ingredient (ai), preferably from 0.1 to 50 g/kg ai.

Other conventional formulation agents may be incorporated into the granules such as buoyancy aids, disintegrants, dispersing agents, binding agents, particularly water soluble binding agents, and surface active agents as well as additional solvents or diluents where necessary.

Suitable dispersants include lignosulphonate dispersants such as sodium lignosulphonate (e.g. "POLYFON H") or naphthalene sulphonate/formaldehyde condensates (e.g. "DISPERSOL T").

Suitable binding agents include polyvinyl pyrrolidone or cellulose such as hydroxypropylcellulose derivatives (e.g. "KLUCEL L").

Suitable surface active agents include anionic surfactants such as dialkylsulphosuccinates (e.g. "AEROSOL OT/B") or sodium lauryl sulphate and non-ionic surface active agents such as alkyl phenol or fatty alcohol ethoxylates e.g. "SYNPERONIC NX".

Additional solvents or liquid diluents for example, aromatic hydrocaleous such as "SOLVESSO 200", alkyl esters or triglycerides may be included to assist dissolution or dispersion of the active ingredient.

The active ingredient (i.e. fungicide, herbicide or plant growth regulator) employed in the composition of the invention will depend upon the particular aquatic environment which they are applied and for what purpose. The compositions are particularly useful for application to rice paddy-fields, and to the active ingredients employed will be those suitable for use in rice crops.

Fungicides for use in the compositions for use in paddy-fields include all fungicidal compounds having a fungicidal effect against diseases which affect a rice plant, for example bacterial leaf blight—(*Xanthomonas campestris* pv. *oryzae*, (*Xanthomonas oryzae*)), blast— (*Pyricularia oryzae*), brown spot—(*Cochliobolus miyabeanus* (*Drechslera oryzae*)), bakanae disease and foot rot—(*Gibberella fujikuroi* (*Fusarium monilforme*)), sheath blight—((*Thanatephorus cucumeris*) (*Rhizoctonia solani*)), and seedling blight—(*Corticium* (*Sclerotium*) *rolfsii*).

As used herein the phrase "fungicidal effect" means that the active ingredient displays activity against a fungal disease at a concentration of 100 ppm, more preferably at 10 ppm. Examples of fungicidal compounds include
1-butyl-1-(2,4-dichlorophenyl)-2-(1,2,4-triazol-1-yl) ethanol (common name hexaconazole), 1-[(2-chlorophenyl)methyl] -1-(1,1-dimethylethyl)-2-(1,2,4-triazol-1-yl)ethanol, 1-(4-fluorophenyl)-1-(2-fluorophenyl)-2-(1,2,4-triazol- 1-yl) ethanol (common name flutriafol), methyl (E)-2-[2-[6-(2-cyanophenoxy)pyrimidin-4-yloxy]phenyl] -3-methoxyacrylate, methyl (E)-2-[2-[6-(2-thioamidophenoxy)pyrimidin- 4-yloxy]phenyl]-3-methoxyacrylate, methyl (E)-2-[2-[6-(2-fluorophenoxy)pyrimidin-4-yloxy] phenyl]-3-methoxyacrylate, methyl (E)-2-[2-[6-(2, 6-difluorophenoxy)pyrimidin- 4-yloxy]phenyl]-3-methoxyacrylate, methyl (E)-2-[2-[3-(pyrimidin-2-yloxy)phenoxy] phenyl]-3-methoxyacrylate, methyl (E)-2-[2-[3-(5-methylpyrimidin- 2-yloxy)phenoxy]phenyl]-3-methoxyacrylate, methyl (E)-2-[ 2-[ 3-(phenylsulphonyloxy)phenoxy]phenyl]- 3-methoxyacrylate, methyl (E)-2-[2-[3-[4-nitrophenoxy]phenoxy] phenyl]-3-methoxyacrylate, methyl (E)-2-[2-phenoxyphenyl]-3-methoxyacrylate, methyl (E)-2-[2-(3,5-dimethylbenzoyl)pyrrol-1-yl]-3-methoxyacrylate, methyl (E)-2-[2-(3-methoxyphenoxy)phenyl]- 3-methoxyacrylate, methyl (E)-2-[2-(2-phenylethen-1-yl)phenyl] -3-methoxyacrylate, methyl (E)-2-(2-[3,5-dichlorophenoxy] pyridin-3-yl)-3-methoxyacrylate, methyl (E)-2-(2-(3-(1,1,2,2-tetrafluoroethoxy)phenoxy)phenyl)-3-methoxyacrylate,
methyl (E)-2-(2-[3-(alpha-hydroxybenzyl)phenoxy] phenyl)-3-methoxyacrylate, methyl (E)-2-(2-(4-phenoxypyridin-2-yloxy)phenyl)-3-methoxyacrylate, methyl (E)-2- [2-(3-n-propyloxyphenoxy)phenyl] -3-methoxyacrylate, methyl (E)-2-[2-(3-isopropyloxyphenoxy)phenyl] -3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]- 3-methoxyacrylate, methyl (E)-2-[2-(4-tert-butylpyridin- 2-yloxy)phenyl]-3-methoxyacrylate, methyl (E)-2-[2-[3-(3-cyanophenoxy)phenoxy] phenyl]-3-methoxyacrylate, methyl (E)-2-[2-(3-methylpyridin-2-yloxymethyl)phenyl] -3-methoxyacrylate, methyl (E)-2-[2-[6-( 2-methylphenoxy)pyrimidin-4-yloxy]phenyl]-3-methoxyacrylate,
methyl (E)-2-[2-(5-bromopyridin-2-yloxymethyl)phenyl] -3-methoxyacrylate, methyl (E)-2-[2-(3-(3-iodopyridin-2-yloxy)phenoxy)phenyl]- 3-methoxyacrylate, methyl (E)-2-[2-[ 6-(2-chloropyridin- 3-yloxy)pyrimidin-4-yloxy]phenyl]-3-methoxyacrylate, (E),(E)-methyl 2-[ 2-(5,6-dimethylpyrazin- 2-ylmethyloximinomethyl)phenyl]-3-methoxyacrylate, (E)-methyl 2-{2-[6-(6-methylpyridin-2-yloxy)pyrimidin- 4-yloxy]phenyl}-3-methoxyacrylate, (E),(E)-methyl 2-{2-(3-methoxyphenyl)methyloximinomethyl]phenyl}- 3-methoxyacrylate, (E)-methyl 2-{2-[6-(2-azidophenoxy)pyrimidin- 4-yloxy]phenyl}-3-methoxyacrylate, (E),(E)-methyl 2-{2-[6-phenylpyrimidin-4-yl)methyloximinomethyl] phenyl}-3-methoxyacrylate, (E),(E)-methyl 2-{2-[(4-chlorophenyl)methyloximinomethyl]phenyl}- 3-methoxyacrylate, (E)-methyl 2-{2-[6-(2-n-propylphenoxy)- 1,3,5-triazin-4-yloxy]phenyl}-3-methoxyacrylate, (E),(E)-methyl 2-{2-[(3-nitrophenyl)methyloximinomethyl]phenyl} -3-methoxyacrylate, (RS)-4-(4-chlorophenyl)-2-phenyl-2-(1H-1,2,4-triazol-1-ylmethyl)butyronitrile, 1-[(2RS,4RS;2RS,4RS)-4-bromo-2-(2,4-dichlorophenyl)tetrahydrofurfuryl] -1H-1,2,4-triazole, 3-(2,4-dichlorophenyl)- 2-(1H-1,2,4-triazol-1-yl)-quinazolin-4(3H)-one, (RS)-2,2-dimethyl-3-(2-chlorobenzyl)-4-(1H-1,2,4 -triazol-1-yl)butan-3-ol, benomyl, bitertanol, blasticidin S, chlorbenzthiazone, chlorothalonil, cycloheximide, cyproconazole, diclobutrazol, diclomezine, difenoconazole, diniconazole, edifenphos, etaconazole, fenapanil, flutolanil, flutriafol, fluzilazole, furconazole-cis, hexaconazole, hydroxyisoxazole, imazalil, iprobenfos, isoprothiolane, kasugamycin, mancozeb, mepronil, metalaxyl, neoasozin, nickel dimethyldithiocarbamate, penconazole, pencycuron, phenazin oxide, phthalide, polyoxin D, probenazole, prochloraz, propiconazole, pyroquilon, streptomycin, techlofthalam, tebuconazole, tetraconazole, thiabendazole, tolclofos-methyl, triadimefon, triadimenol, tricyclazole and validamycin A.

Suitable herbicides for use in the compositions for use in paddy-fields are those which are selective for use in rice crops. These include benzo-2,1,3-thiodiazin-4 -one-2,2-dioxides such as 3-isopropylbenzo-2,1,3 -thiadiazin-4-one-2, 2-dioxide (bentazon); rice selective hormone herbicides, particularly the phenoxy alkanoic acids such as 4-chloro-2-methylphenoxy acetic acid (MCPA), 2,4-dichlorophenoxyacetic acid (2,4-D), 2-(4-chloro-2-methylphenoxy) propionic acid (mecoprop), and their derivatives (e.g. salts, esters and amides); rice selective phenoxypropionate herbicides such as 2-(4-(5 -trifluoromethyl)-2-(pyridinyl)oxy) phenoxypropanoic acid (fluazifop) and esters thereof, 2-(4-(3-chloro-5 -trifluoro-methyl)-2-pyridinyl)oxy)phenoxy)propanoic acid (haloxyfop) and esters thereof, and (+)-2-[4-(6-chlorobenzoxazol- 2-yloxy)phenoxy]propionic acid (fenoxaprop) and esters thereof such as the ethyl ester; and rice selective sulfonyl urea herbicides such as (4,6-dimethoxypyrimidin- 2-ylcarbamoylsuphamoy)-O-toluic acid (benzsulfuron) and esters thereof such as the methyl3-[3-(4-methoxy-6 -methyl-1,3,5-triazin-2-yl)-ureidosulphonyl] thiophene-2-carboxylate(DPX-M6313), and 5-(4,6-dimethoxypyrimidin-2-ylcarbamoylsulphamoyl)-1 -methylpyrazole-4-carboxylic acid (pyrazosulfuron).

Particular herbicidal active ingredients which are useful in the compositions of the present invention are phenoxypropionate herbicides and these include compounds described in EP-A-44163 and EP-A-248554 in addition to those mentioned above.

Suitable herbicides in EP-248554-A are those of formula (I):

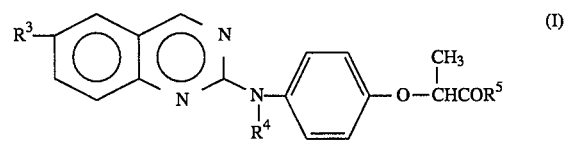

and R-enantiomers thereof;
wherein $R^3$ is halogen, $CF_3$ or methyl;
$R^4$ is methyl or ethyl; and
$R^5$ is $OR^6$ or $—NHSO_2R^7$ wherein $R^6$ is hydrogen, optionally substituted $C_{1-10}$ alkyl, optionally substituted $C_{2-10}$ alkenyl, optionally substituted $C_{2-10}$ alkynyl, $C_{3-6}$ cycloalkyl, optionally substituted aryl or a cation, and $R^7$ is $C_{1-10}$ alkyl or halo $C_{1-10}$ alkyl.

Particular compounds of formula (I) described in EP-A-248554 are those set out in Table I below.

TABLE I

| Compound No | $R^3$ | $R^4$ | $R^5$ |
|---|---|---|---|
| 1* | —Cl | —CH$_3$ | —O—CH$_2$CH$_3$ |
| 2* | —F | —CH$_3$ | —O—CH$_2$CH$_3$ |
| 3 | —Cl | —CH | —O—(CH$_2$)$_2$CH$_3$ |
| 4 | —Cl | —CH$_3$ | —OCH(CH$_3$)$_2$ |
| 5 | —Cl | —CH$_2$CH$_3$ | —O—CH$_2$CH$_3$ |
| 6 | —CH$_3$ | —CH$_3$ | —O—CH$_2$CH$_3$ |
| 7 | —F | —CH$_3$ | —OH |
| 8 | —F | —CH$_3$ | —O—CH$_2$CH$_3$ |
| 9 | —F | —CH$_3$ | —O—CH$_3$ |
| 10 | —CF$_3$ | —CH$_3$ | —O—CH$_2$CH$_3$ |
| 11 | —Cl | —CH$_3$ | —OH |
| 12 | —Br | —CH$_3$ | —OH |
| 13 | —Br | —CH$_3$ | —O—CH$_2$CH$_3$ |
| 14 | —Cl | —CH$_3$ | —O—CH$_3$ |
| 15* | Cl | CH$_3$ | —O—(CH$_2$)$_3$CH$_3$ |
| 16* | Cl | CH$_3$ | —O—CHCH$_2$CH$_3$ (CH$_3$) |
| 17* | Cl | CH$_3$ | —O—CH$_2$C(CH$_3$)$_3$ |
| 18* | Cl | CH$_3$ | —O—CH$_2$CH=CH$_2$ |
| 19* | Cl | CH$_3$ | —OH |
| 20* | Cl | CH$_3$ | —O—CH$_2$C≡CH |
| 21* | Cl | CH$_3$ | —O—(CH$_2$)$_2$OCH$_3$ |
| 22* | Cl | CH$_3$ | —O—CH$_2$— |
| 23* | Cl | CH$_3$ | —O—(CH$_2$)$_2$—O—CH$_2$— |
| 24* | Cl | CH$_3$ | —O——NO$_2$ |
| 25* | Cl | CH$_3$ | —NSO$_2$CH$_3$ \| H |
| 26* | Cl | CH$_3$ | ⊕N(CH$_2$CH$_2$OH)$_3$ \| H |
| 27* | Cl | CH$_3$ | —O—CH$_2$CH(CH$_3$)$_2$ |
| 28* | Cl | CH$_3$ | —O—(CH$_2$)$_4$CH$_3$ |
| 29* | Cl | CH$_3$ | CH$_3$ \| —O—CH(CH$_2$)$_2$CH$_3$ |
| 30* | Cl | CH$_3$ | CH$_3$ \| —O—CH$_2$CH—CH$_2$CH$_3$ |
| 31* | Cl | CH$_3$ | —O—(CH$_2$)$_2$—CH—(CH$_3$)$_2$ |
| 32* | Cl | CH$_3$ | CH$_3$ \| —O—CH—CH(CH$_3$)$_2$ |
| 33* | Cl | CH$_3$ | —O—CH$_2$— |
| 34* | Cl | CH$_3$ | —O—CH(CH$_3$)$_2$ |
| 35* | Cl | CH$_3$ | CH$_3$ \| —O—CH—CH$_2$OCH$_3$ |
| 36* | Cl | CH$_3$ | —O—CH$_2$—CH—CH$_3$ \| OCH$_3$ |
| 37* | Cl | CH$_3$ | OCH(CH$_2$CH$_3$)$_2$ |
| 38* | Cl | CH$_3$ | OCH$_2$Si(CH$_3$)$_3$ |

Compounds marked * in Table I are in the form of the R-enantiomer substantially free of the S-enantiomer.

Combinations of more than one active ingredient ie fungicide, herbicide, and plant growth regulatory agent, may be incorporated into the compositions of the invention. For example a compound of formula (I) may be combined with another herbicide for example a sulphonyl urea or a different phenoxypropionate herbicide, in particular those listed above.

Suitable plant growth regulators for use in the compositions in rice paddy-fields include α-(1-methylethyl)-α-(phenylethynyl)-5-pyrimidine methanol, β-[(4-chlorophenyl)methyl]-α-(1,1-dimethylethyl)- 1H-1,2,4-triazole-1-ethanol (common name paclobutrazol), 1-phenyl-imidazole-5-carboxylic acid derivatives such as (1-(2,6-diethylphenyl)-imidazole-5-carboxamide and ethyl-4-cyclopropyl(hydroxy)methylene-3,5-dioxocyclohexanecarboxylate.

Other suitable plant growth regulating compounds may be those described for example in U.S. Pat. No. 4,560,403 and EP-A-281120.

It is important that the oil employed in the composition is either miscible with the desired active ingredient or has properties such that the active ingredient can be dispersed in it, and this can be readily determined by simple routine tests. Furthermore in order to ensure that the active ingredient remains on the surface of the water, the specific gravity of the oil must be low, i.e. less than 1 (preferably below 0.9). However, although the active ingredient is on the water surface, it may sink if the carrier is too volatile. Hence the oil, or the oil as modified by the presence of the fungicidal, herbicidal or plant growth regulating active ingredient, must have a low volatility, as indicated by a boiling point of greater than 150° C., preferably above 200° C., and more preferably above 250° C.

Suitably the oil comprises one or more of a straight or branched chain, saturated or unsaturated $C_{8-18}$ alcohol or a lower alkyl ester of a straight or branched chain, saturated or unsaturated $C_{8-18}$ monocarboxylic acid. In particular the alcohols preferably contain from 12–18 carbon atoms.

Suitable oils are oleyl alcohol, decyl alcohol, tridecyl alcohol and Synprol (Synprol is a registered trade mark for a synthetic mixture of mainly straight chain $C_{13-15}$ alcohols). Other suitable oils include soya bean oil, lower alkyl esters, of oleic acid, lauric acid or mixed fatty acids of natural origin, for example coconut oil fatty acid. The term lower alkyl as used herein refers to straight or branched chain alkyl groups containing from 1 to 4 carbon atoms.

The compositions according to the invention are most suitably prepared in the form of granules using conventional processes for granule formulation such as extrusion, agglomeration, impregnation, spheronisation or coating, for example on pumice or sand.

When the composition of the invention comprises a dispersion of active ingredient in a suitable oil, it can be prepared for example by mixing the solid active ingredient and a surfactant or dispersant with a suitable low viscosity processing liquid (for example Isopar L) in which the active ingredient is not soluble. To this mixture are added suitable beads (such as zirconium oxide beads or glass beads) and the resulting mixture is agitated in suitable manner (such as milling) until the average particle size is for example between $5 \times 10^{-7}$ m and $4 \times 10^{-6}$ m. The beads are then separated off and the resulting suspension is mixed with a suitable low volatile oil (for example soya bean oil) in which the active ingredient is also insoluble. The resulting mixture is coated onto suitable preformed granules (suitably made of sodium sesquicarbonate ("CREX"), or other water soluble salts.

When the composition comprises a solution of active ingredient in an oil, it can be prepared in a number of ways. For example, the solution can be formed by dissolving the active ingredient in the oil, if necessary in the presence of a volatile solvent (for example 1,1,1-trichloroethane GENKLENE) to aid dissolution. Where necessary a surfactant may also be present.

The resultant solution can then be impregnated into suitable preformed granules which are then dried. Preformed granules may comprise a suitable substrate such as sodium sesquicarbonate or they may be prepared for example by non-aqueous extrusion of a suitable solid substrate.

Alternatively the solution optionally in the presence of water, may be mixed with the desired solid components of the granule to form a paste which is then extruded using conventional granule extruding equipment (for example a Fuji Paudal granulator). The resulting granules are then dried to remove any volatile components and graded by sieving to remove under or over sized particles.

In some instances it may be possible to prepare an extrudable paste directly by mixing all components of the granule together.

The following Examples illustrate the preparation of typical formulations according to the invention. In the Examples, active ingredients are referred to as indicated below:

Compound A: methyl (E)-[2-[6-(2-cyanophenoxy)pyrimidin- 4-yloxy]phenyl]-3-methoxyacrylate Compound B: methyl (E)-2-[2-[3-(pyrimidin-2-yloxy)phenoxy] phenyl]-3-methoxyacrylate.

Compound C: Compound no 1 in Table I.

EXAMPLE 1

| Ingredients | % W/W |
| --- | --- |
| Active ingredient (Compound A) | 1.0 |
| Aromatic hydrocarbon solvent ("SOLVESSO 200") | 2.0 |
| Methyl oleate | 2.0 |
| Sodium sesquicarbonate ("CREX") | to 100.0 |

Granules were prepared by solvent impregnation of a preformed granule base using a solution of active ingredient, methyl oleate and aromatic hydrocarbon solvent in 1,1,1-trichloroethane ("GENKLENE") They were then dried to remove the volatile 1,1,1-trichloroethene.

EXAMPLE 2

| Ingredients | % W/W |
| --- | --- |
| Active ingredient (Compound B) | 1.0 |
| Surfactant B246 | 0.05 |
| Soya bean oil | 7.5 |
| Sodium sesquicarbonate ("CREX") | to 100.0 |

The active ingredient and surfactant were mixed with Isopar L. After the addition of zirconium oxide beads the mixture was shaken until the average particle size was of the order of $3 \times 10^{-6}$ m. The zirconium oxide beads were separated and the resulting suspension was mixed with soya bean oil. This was coated onto preformed "CREX" granules.

EXAMPLE 3

This Example describes the manufacture of extruded granules with a water-soluble base. The composition of the granules was:

| | g/kg |
| --- | --- |
| Compound C | x |
| Oleyl alcohol | 50 |
| Sodium sesquicarbonate | to 1 kg. |

(where x gives 0.1 to 20 g/kg ai in particular 0.5, 1.0, 2.1, 4.2 and 8.3 g/kg)

The composition is mixed using a solution or suspension of active ingredient in oleyl alcohol to form an extrudable paste which is then forced through perforated screens of the required size to form cylindrical granules which are then sieved to the required size range.

EXAMPLE 4

This Example describes the manufacture of an effervescent agglomerated granule. The composition of the granule was:

| | g/kg |
| --- | --- |
| Compound C | x |
| oleyl alcohol | 50 |
| Hydroxypropyl cellulose (binding agent) | 15 |
| Sodium lignosulphonate (binding agent) | 26 |
| Sodium sesquicarbonate {effervescent} | 210 |
| Adipic acid {mix} | 290 |
| Magnesium sulphate | to 1 kg | x gives 0.1–20 g/kg ai.

The granules were formed by mixing the components in a rotating pan so that they formed essentially spherical granules.

EXAMPLE 5

The following agglomerated granules were prepared using a method as described in Example 4. The composition of the granules was:

| | g/kg |
|---|---|
| Compound C | x |
| Methyl oleate | 50 |
| Magnesium sulphate | to 1 kg |

Agglomerated granule: x is in the range of 0.1 to 20 g/kg ai.

EXAMPLE 6

The following effervescent granules were prepared as described in Example 4. The composition of the granules was:

| | g/kg |
|---|---|
| Compound C | x |
| Oleyl alcohol | 50 |
| Polyfan H | 25 |
| AEROSOL TO/B | 25 |
| Hydroxypropyl cellulose | 15 |
| Adipic acid | 275 |
| Sodium sesquicarbonate | 197 |
| Magnesium sulphate (anhydrous) | to 1 kg | where x is from 0.8 to 6.7 g/Kg

EXAMPLE 7

Large gravel trays (approx. 60×32 cm) of 'Minster' JIP No. 1 were densely sown with 'Koshi' rice seed. When the seedlings were 12 days old they were transplanted into 12 cm diameter sealed pots also containing 'Minster' JIP No. 1, four seedlings evenly spaced in each pot. They were top watered and placed in a 24° C. glasshouse. The plants remained in the glasshouse for 12 days to enable the roots to become established. 48 hours prior to treatment the pots were flooded with tap water to a depth of 2 cm.

The pots were randomly labelled and granules (made according to Example 2) to give a coverage equivalent to 3000 g of active ingredient per hectare, were carefully sprinkled on to the surface of the water and around the pots and plants. The water level was topped up 48 hours after treatment and kept constant for the duration of the test.

14 Days after treatment the plants were sprayed with a spore suspension of *Pyricularia oryzae* at 200,000 sp/ml in 0.05% Tween 20. The plants were incubated at 24° C. in a humidity cabinet before being returned to the glasshouse to await assessment.

The disease control is shown in Table II.

TABLE II

| Compound No | Percentage Disease Control |
|---|---|
| 2 | 100 |

EXAMPLE 8

Test units were prepared each comprising a 7" diameter pot containing compost (Mendip loam). Test species were the japonica rice variety Ishikari (Rc-Is) and the grass weed *Echinochloa crus-galli* (Ec). Three rice plants and three plants of *E. crus-galli* were transplanted into each unit at an interval of 6 days before treatment. Test units were kept damp until 1 or 2 days before treatment when a 3 cm deep flood was established in all test units. This was maintained for the duration of the test. At treatment the rice plants were at a 2–2½ leaf growth stage and the *E. crus-galli* at 2½–3 leaves.

Granules in accordance with Example 6 were prepared but having various concentrations of active ingredient. The concentrations were such that a uniform application rate of 30 kg granules per hectare achieved the desired concentration of active ingredient. The granules were applied by hand using a spatula. They were distributed evenly around the floodwater in each test unit. An early assessment of rice damage was made after 9 days. Assessments of rice damage and weed control were made at 27 days after treatment. Results are shown in Table III and are the mean of 3 replicates.

TABLE III

| Rate of application of Compound C g/Ha | % Damage to Plants | | |
|---|---|---|---|
| | Rc-Is | | Ec |
| | 9 DAT* | 27 DAT* | 27 DAT* |
| 25 | 0 | 0 | 98 |
| 50 | 0 | 0 | 95 |
| 100 | 0 | 0 | 100 |
| 200 | 0 | 0 | 100 |

DAT - Days after treatment.

We claim:

1. A granular fungicidal composition for application to an aquatic environment, the composition comprising a solid carrier, methyl (E)-2-[2-[6-(2 -cyanophenoxy)pyrimidin-4-yloxylphenyl]-3-methoxyacrylate as a fungicidal active ingredient, and an oil with which the said active ingredient is miscible or in which it is capable of being dispersed, said oil being water-immiscible, having a specific gravity of less than 1 and a boiling point at atmospheric pressure of greater than 150° C., and the oil comprises one or more of a straight or branched chain, saturated or unsaturated $C_{8-18}$ alcohol or a lower alkyl ester of a straight or branched chain, saturated or unsaturated $C_{8-18}$ monocarboxylic acid.

2. A fungicidal composition according to claim 1 wherein the oil has a boiling point of greater than 200° C.

3. A fungicidal composition as claimed in claim 1 wherein the oil comprises one or more of oleyl alcohol, decyl alcohol, tridecyl alcohol, Synprol and the methyl, ethyl, propyl or isopropyl ester of oleic acid, lauric acid or mixed fatty acids of natural origin.

4. A fungicidal composition as claimed in claim 1 wherein the granule further comprises effervescence-initiating compounds.

5. A composition as claimed in claim 1 having a fungicidal effect against one or more of the following diseases:

bacterial leaf blight—(*Xanthomonas campestris* pv. *oryzae* (*Xanthomonas oryzae*)), blast—(*Pyricularia oryzae*), brown spot—(*Cochliobolus miyabeanus* (*Drechslera oryzae*)), bakanae disease and foot rot—((*Gibberella fujikuroi*) (*Fusarium moniliforme*)), sheath blight—((*Thanatephorus cucumeris*) (*Rhizoctonia solani*)), and seedling blight—(*Corticium* (*Sclerotium*) *rolfsii*).

6. A method of controlling fungal growth on plants growing in an aquatic environment which method comprises applying to the aquatic environment in which the plant is cultivated an effective amount of a fungicidal composition as claimed in claim 1.

7. A method according to claim 6 wherein the aquatic environment is a rice paddy field.

* * * * *